(12) United States Patent
Ueda (10) Patent No.: US 11,469,150 B2
(45) Date of Patent: *Oct. 11, 2022

(54) DEVICE AND FORMING METHOD OF DEVICE

(71) Applicant: JAPAN AVIATION ELECTRONICS INDUSTRY, LIMITED, Tokyo (JP)

(72) Inventor: Shinji Ueda, Tokyo (JP)

(73) Assignee: JAPAN AVIATION ELECTRONICS INDUSTRY, LIMITED, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/152,877

(22) Filed: Jan. 20, 2021

(65) Prior Publication Data

US 2021/0280485 A1 Sep. 9, 2021

(30) Foreign Application Priority Data

Aug. 3, 2020 (JP) .............................. JP2020-131420

(51) Int. Cl.
*H01L 23/31* (2006.01)
*H01L 21/56* (2006.01)
(Continued)

(52) U.S. Cl.
CPC .......... *H01L 23/3142* (2013.01); *H01L 21/56* (2013.01); *H01L 23/5385* (2013.01); *H01L 23/5386* (2013.01); *H01L 25/0657* (2013.01)

(58) Field of Classification Search
CPC . H01L 23/3142; H01L 21/56; H01L 23/5385; H01L 23/5386; H01L 25/0657; H01L 21/67103; H01L 21/67126
See application file for complete search history.

(56) References Cited

U.S. PATENT DOCUMENTS 6,045,652 A 4/2000 Tuttle et al.
7,033,857 B2 4/2006 Munakata et al.
(Continued)

FOREIGN PATENT DOCUMENTS

JP 2001332654 A 11/2001
JP 2007287635 A 11/2007
(Continued)

OTHER PUBLICATIONS

Extended European Search Report (EESR) dated Jul. 15, 2021, issued in European Application No. 21152624.
(Continued)

*Primary Examiner* — Nicholas J Tobergte
(74) *Attorney, Agent, or Firm* — Holtz, Holtz & Volek PC (57) ABSTRACT

A device comprises: a first film having a first inner portion, a first seal portion and a first contact portion; a second film having a second inner portion, a second seal portion and a second contact portion; a first circuit member having a first contact point; and a second circuit member having a second contact point. The first seal portion and the second seal portion are bonded together. The first contact portion and the second contact portion are in contact with each other in a contact region which surrounds the first inner portion and the second inner portion throughout their entire circumference. The first circuit member and the second circuit member are shut in a closed space which is enclosed by the first inner portion and the second inner portion. The first contact point and the second contact point are in contact with each other.

13 Claims, 9 Drawing Sheets

(51) Int. Cl.
*H01L 23/538* (2006.01)
*H01L 25/065* (2006.01)

(56) References Cited

U.S. PATENT DOCUMENTS

| | | | |
|---|---|---|---|
| 9,276,234 | B2 | 3/2016 | Park |
| 10,202,525 | B2 | 2/2019 | Park et al. |
| 2001/0007335 | A1 | 7/2001 | Tuttle et al. |
| 2006/0033188 | A1 | 2/2006 | Chen et al. |
| 2010/0230151 | A1 | 9/2010 | Michalk |
| 2013/0115735 | A1 | 5/2013 | Chen et al. |
| 2014/0110685 | A1 | 4/2014 | Hong et al. |
| 2018/0358770 | A1* | 12/2018 | Light .............. H01R 43/205 |
| 2019/0252130 | A1* | 8/2019 | Hasegawa .......... H01G 11/70 |
| 2020/0028145 | A1 | 1/2020 | Kano et al. |
| 2020/0220055 | A1 | 7/2020 | Kitaura et al. |
| 2022/0037174 | A1* | 2/2022 | Hashiguchi ...... H01L 21/67126 |

FOREIGN PATENT DOCUMENTS

| | | | |
|---|---|---|---|
| JP | 2010287635 A | 12/2010 |
| JP | 2018186064 A | 11/2018 |
| TW | 201338236 A | 9/2013 |
| TW | 201438307 A | 10/2014 |
| TW | 201518457 A | 5/2015 |
| TW | 201818581 A | 5/2018 |
| TW | 201843777 A | 12/2018 |
| TW | 201913829 A | 4/2019 |

OTHER PUBLICATIONS

Taiwanese Office Action and Search Report (and English language translation thereof) dated Dec. 9, 2021, issued in counterpart Taiwanese Application No. 110100938.
Related U.S. Appl. No. 17/153,298; First Named Inventor: Osamu Hashiguchi; Title: "Device and Forming Method of Device", filed Jan. 20, 2021.
Taiwanese Office Action (and English language translation thereof) dated Oct. 5, 2021, issued in counterpart Taiwanese Application No. 110100939 (which is a Taiwanese counterpart of related U.S. Appl. No. 17/153,298).
Notice of Allowance dated Dec. 27, 2021, issued in related U.S. Appl. No. 17/153,298.

* cited by examiner

DEVICE AND FORMING METHOD OF DEVICE

CROSS REFERENCE TO RELATED APPLICATIONS

This application is based on and claims priority under 35 U.S.C. § 119 to Japanese Patent Applications No. JP 2020-047177 filed Mar. 18, 2020 and No. JP 2020-131420 filed Aug. 3, 2020, the contents of which are incorporated herein in their entirety by reference.

BACKGROUND OF THE INVENTION

This invention relates to a device comprising a circuit member sealed by a film.

For example, a device which can be made thinner is disclosed in JP2001-332654A (Patent Document 1), the content of which is incorporated herein by reference.

Figure 17:
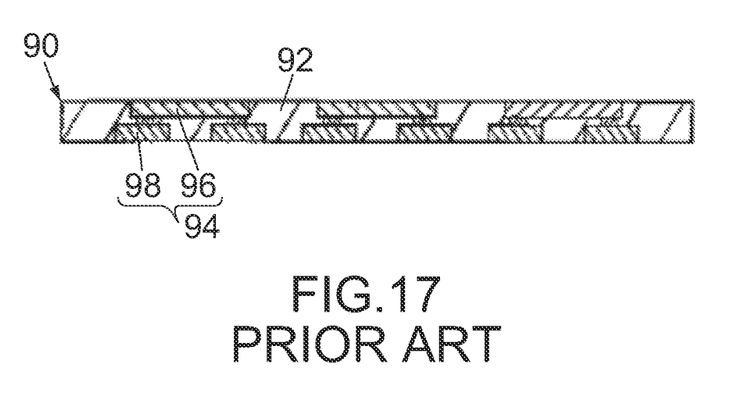
FIG. 17 is a cross-sectional view showing a device of Patent Document 1.

Referring to FIG. 17, Patent Document 1 discloses a module (device) 90 with built-in semiconductor chips. The device 90 comprises a thermosetting resin composition (sealing resin) 92 and a circuit member 94 including semiconductor chips 96 and wiring patterns 98. The sealing resin 92 is formed so that the circuit member 94 is embedded therewithin. Then, a surface of the sealing resin 92 is polished so that the device 90 is made thinner.

Further reduction in thickness is required for a device comprising a circuit member.

SUMMARY OF THE INVENTION

It is therefore an object of the present invention to provide a new device which can be made thinner.

An aspect of the present invention provides a device comprising a first film, a second film, a first circuit member and a second circuit member. The first film has a first inner portion and a first outer portion. The first inner portion is located inward of the first outer portion. The second film has a second inner portion and a second outer portion. The second inner portion is located inward of the second outer portion. The first outer portion has a first seal portion and a first contact portion. The second outer portion has a second seal portion and a second contact portion. The first seal portion and the second seal portion are bonded together to form a seal trace. The first contact portion and the second contact portion are in contact with each other in a contact region. The contact region surrounds the first inner portion and the second inner portion throughout their entire circumference. The device is formed with a closed space which is enclosed by the first inner portion and the second inner portion. The first circuit member and the second circuit member are shut in the closed space. The first circuit member has a first contact point. The second circuit member has a second contact point. The first contact point and the second contact point are in contact with each other.

Another aspect of the present invention provides a forming method of a device comprising a first film, a second film, a first circuit member and a second circuit member. The forming method comprises a preparing step, an arranging step and a sealing step. In the preparing step, the first film, the second film, the first circuit member and the second circuit member are prepared. The first circuit member comprises a first contact point. The second circuit member comprises a second contact point. In the arranging step, the first film, the first circuit member, the second circuit member and the second film, which are stacked in this order, are arranged in a chamber while the first contact point and the second contact point face each other. In the sealing step, the first film and the second film are sealed under a state where the chamber is vacuumed, so that the first circuit member and the second circuit member are shut in a closed space enclosed by the first film and the second film, and the first contact point and the second contact point are brought into contact with each other.

According to the device of an aspect of the present invention, the first film and the second film overlap with each other to be in contact with each other while the first circuit member and the second circuit member (hereafter, simply referred to as "circuit members") are sandwiched therebetween. The structure of each of the circuit members is not restricted except that each of the circuit members should be provided with the contact point. Thus, each of the circuit members of an aspect of the present invention has a simple structure and can be formed of various material. For example, each of the circuit members may be an insulation film formed with a conductive pattern having the contact point. In this instance, the thickness of the entire device can be made extremely thin. Thus, an aspect of the present invention provides a new device which can be made thinner.

An appreciation of the objectives of the present invention and a more complete understanding of its structure may be had by studying the following description of the preferred embodiment and by referring to the accompanying drawings.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DESCRIPTION OF PREFERRED EMBODIMENTS

Figure 1:
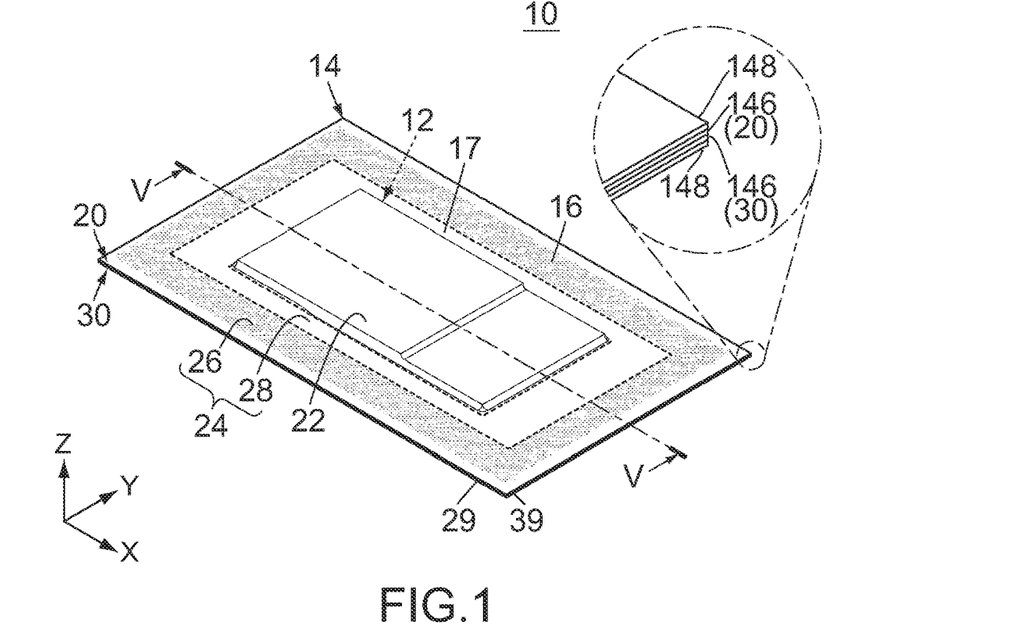
FIG. 1 is a perspective view showing a device according to an embodiment of the present invention, wherein boundary lines of a contact region formed between a first film and a second film are illustrated with dashed line, and a part of the device enclosed by chain dotted lines is enlarged and illustrated.

Referring to FIG. 1, a device 10 according to an embodiment of the present invention is an independent electronic device. More specifically, the device 10 can work solely without physically attached to another electronic device (not shown). For example, the device 10 measures the heart rate of a subject by attaching the device 10 near the heart of the subject, and transmits the measurement result to another electronic device. Thus, the device 10 can be used as an electronic device for measuring biological information such as heart rate. However, the present invention is not limited thereto but is applicable to various devices having various functions.

The device 10 of the present embodiment comprises a circuit structure 12 and a film member 14. The circuit structure 12 is a member for enabling the device 10 to work as an electronic device. For example, the circuit structure 12 has an electronic circuit (not shown) for measuring heart rate and another electronic circuit (not shown) for transmitting the measurement result to another electronic device (not shown). The film member 14 entirely accommodates the circuit structure 12 therewithin and protects the circuit structure 12 from an external environment. Thus, the circuit structure 12 is shut in the film member 14.

Hereafter, explanation will be made about the structure of the device 10 of the present embodiment.

Figure 2:
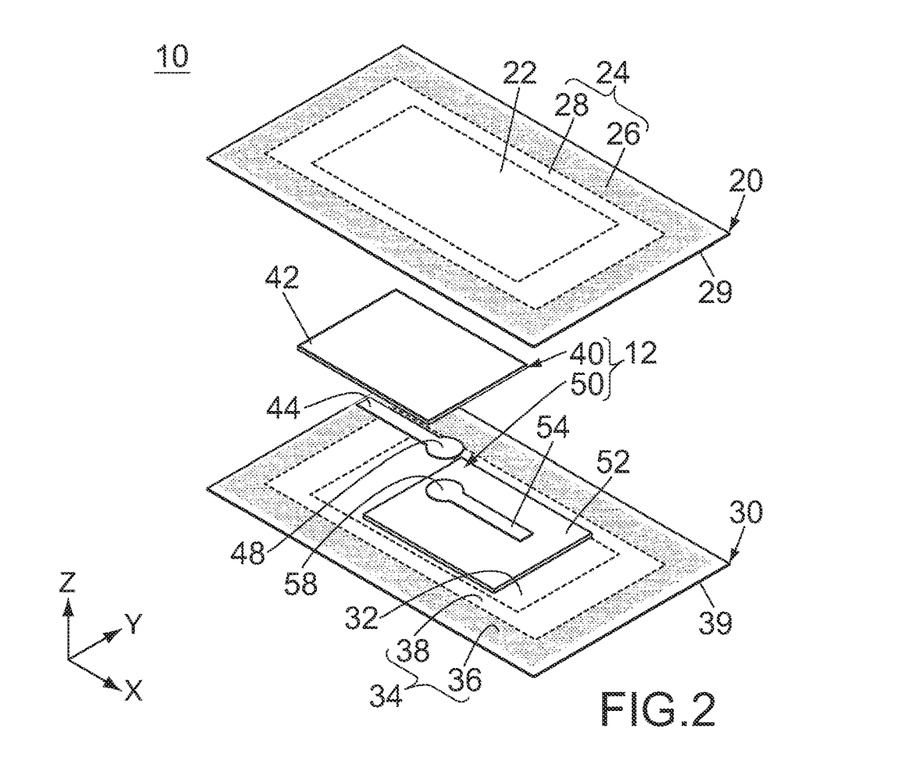
FIG. 2 is an exploded, perspective view showing the device of FIG. 1, wherein the boundary lines of the contact region of each of the first film and the second film are illustrated with dashed line.

Referring to FIG. 2, the circuit structure 12 of the present embodiment comprises a first circuit member 40 and a second circuit member 50. The film member 14 of the present embodiment comprises a first film 20 made of insulator and a second film 30 made of insulator. Thus, the device 10 comprises the first film 20, the second film 30, the first circuit member 40 and the second circuit member 50. The aforementioned four members, i.e., the first film 20, the second film 30, the first circuit member 40 and the second circuit member 50, are stacked in an upper-lower direction (Z-direction) and are combined to form one of the device 10 (see FIG. 1). The device 10 of the present embodiment comprises only the aforementioned four members. However, the present invention is not limited thereto, but the device 10 may further comprise another member in addition to the aforementioned four members. For example, the device 10 may further comprise an additional circuit member.

Figure 3:
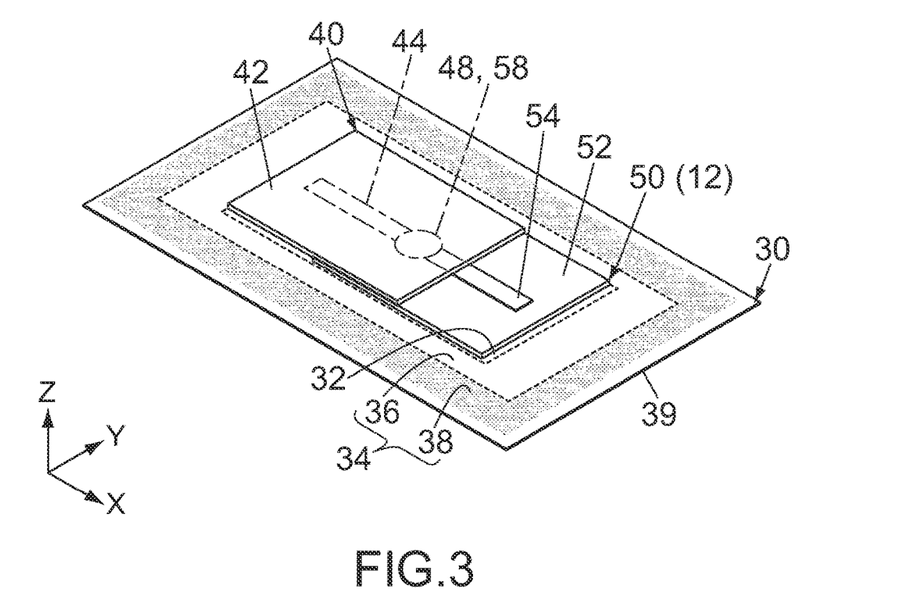
FIG. 3 is a perspective view showing the device of FIG. 1, wherein the first film is not illustrated, the boundary lines of the contact region of the second film are illustrated with dashed line, and outlines of a hidden first conductive pattern and a hidden second conductive pattern are illustrated with chain dotted lines.

Referring to FIGS. 2 and 3, the first circuit member 40 of the present embodiment has a first base portion 42 and a first conductive pattern 44. The first base portion 42 of the present embodiment is a thin, rectangular sheet formed of an insulation film and is bendable. The first base portion 42 extends in parallel to a horizontal plane (sheet plane: XY-plane) perpendicular to the Z-direction. The first conductive pattern 44 is formed on the first base portion 42. In detail, the first conductive pattern 44 is made of conductor such as copper and is formed on a lower surface (negative Z-side surface) of the first base portion 42 by a forming method such as silver ink printing or etching.

The second circuit member 50 of the present embodiment has a second base portion 52 and a second conductive pattern 54. The second base portion 52 of the present embodiment is a thin, rectangular sheet formed of a film and is bendable. The second base portion 52 extends in parallel to the XY-plane. The second conductive pattern 54 is formed on the second base portion 52. In detail, the second conductive pattern 54 is made of conductor such as copper and is formed on an upper surface (positive Z-side surface) of the second base portion 52 by a forming method such as silver ink printing or etching.

Each of the first circuit member 40 and the second circuit member 50 of the present embodiment has the aforementioned structure. However, the present invention is not limited thereto. For example, the shape of each of the first base portion 42 and the second base portion 52 is not limited to be rectangular but can be modified as necessary. Each of the first base portion 42 and the second base portion 52 may be a rigid circuit board. The forming method of each of the first conductive pattern 44 and the second conductive pattern 54 is not specifically limited, provided that each of the first conductive pattern 44 and the second conductive pattern 54 is made of conductor.

In the present embodiment, the first conductive pattern 44 has a first contact point 48, and the second conductive pattern 54 has a second contact point 58. Thus, the first circuit member 40 comprises the first contact point 48, and the second circuit member 50 comprises the second contact point 58. In the fabricated device 10 (see FIG. 1), the first contact point 48 and the second contact point 58 are in contact with each other (see chain dotted lines in FIG. 3). Thus, the first circuit member 40 and the second circuit member 50 are combined to each other so that the first contact point 48 and the second contact point 58 are brought into contact with each other. The first circuit member 40 and the second circuit member 50 combined as described above form the circuit structure 12. The first conductive pattern 44 and the second conductive pattern 54 of the circuit structure 12 are electrically connected with each other.

The first conductive pattern 44 and the second conductive pattern 54 illustrated in FIGS. 2 and 3 are abstract conductive patterns for simple explanation about the present invention and have no specific function. In other words, even when the illustrated first contact point 48 and the illustrated second contact point 58 are brought into contact with each other, the device 10 (see FIG. 1) does not work as an electronic device. The actual first conductive pattern 44 and the actual second conductive pattern 54 have the structure illustrated in FIG. 4, for example.

Figure 4:
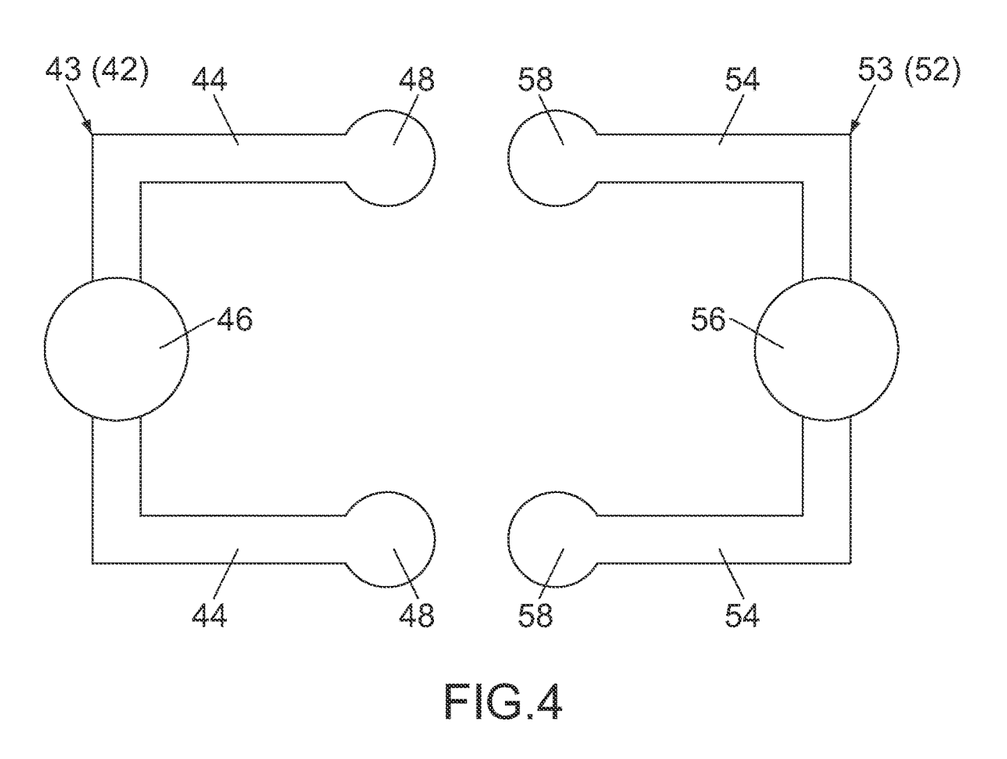
FIG. 4 is a view showing specific examples of the first conductive pattern of a first circuit member and the second conductive pattern of a second circuit member of FIG. 3.

Referring to FIG. 4, the first base portion 42 has a first circuit 43 formed on a lower surface thereof, and the second base portion 52 has a second circuit 53 formed on an upper surface thereof. The first circuit 43 has a coin battery 46 and two of the first conductive patterns 44 which are formed with the first contact points 48, respectively. The second circuit 53 has a light emitting diode (LED) 56 and two of the second conductive patterns 54 which are formed with the second contact points 58, respectively. When the first contact points 48 are brought into contact with the second contact points 58, respectively, the coin battery 46 supplies electric power to the LED 56, and the LED 56 emits light. The structure of the first circuit 43 and the second circuit 53 can be modified to a more practical structure than that of the example of FIG. 4. For example, the second circuit 53 may have, instead of the LED 56, a circuit for measuring heart rate and another circuit for transmitting the measurement results.

According to the example of FIG. 4, each of the number of the first contact points 48 and the number of the second contact points 58 is two. However, each of the number of the first contact points 48 and the number of the second contact points 58 may be one as shown in FIG. 2 or may be three or more. Thus, referring to FIGS. 2 and 3, the first circuit member 40 should have one or more of the first contact points 48, and the second circuit member 50 should have one or more of the second contact points 58 which correspond to the first contact points 48, respectively. In the fabricated device 10 (see FIG. 1), each of the first contact points 48 should be in contact with the corresponding second contact point 58.

Referring to FIG. 2, the first film 20 and the second film 30 of the present embodiment have structures similar to each other. More specifically, each of the first film 20 and the second film 30 is a thin, rectangular sheet formed of an insulation film and is bendable. Each of the first film 20 and the second film 30 extends in parallel to the XY-plane. The first film 20 has a peripheral edge 29 in the XY-plane. The second film 30 has a peripheral edge 39 in the XY-plane.

Referring to FIG. 1 together with FIG. 2, the first film 20 and the second film 30 of the present embodiment overlap with each other so that the position of the peripheral edge 29 and the position of the peripheral edge 39 are aligned with each other in the XY-plane. However, the present invention is not limited thereto. For example, the size of the first film 20 in the XY-plane and the size of the second film 30 in the XY-plane may be different from each other. The shape of each of the first film 20 and the second film 30 is not limited to be rectangular but can be modified as necessary.

Referring to FIG. 2, the first film 20 has a first inner portion 22 and a first outer portion 24. The first inner portion 22 is located inward of the first outer portion 24 in the XY-plane. In other words, the first outer portion 24 is a part of the first film 20 which surrounds the first inner portion 22. The second film 30 has a second inner portion 32 and a second outer portion 34. The second inner portion 32 is located inward of the second outer portion 34 in the XY-plane. In other words, the second outer portion 34 is a part of the second film 30 which surrounds the second inner portion 32.

Figure 5:
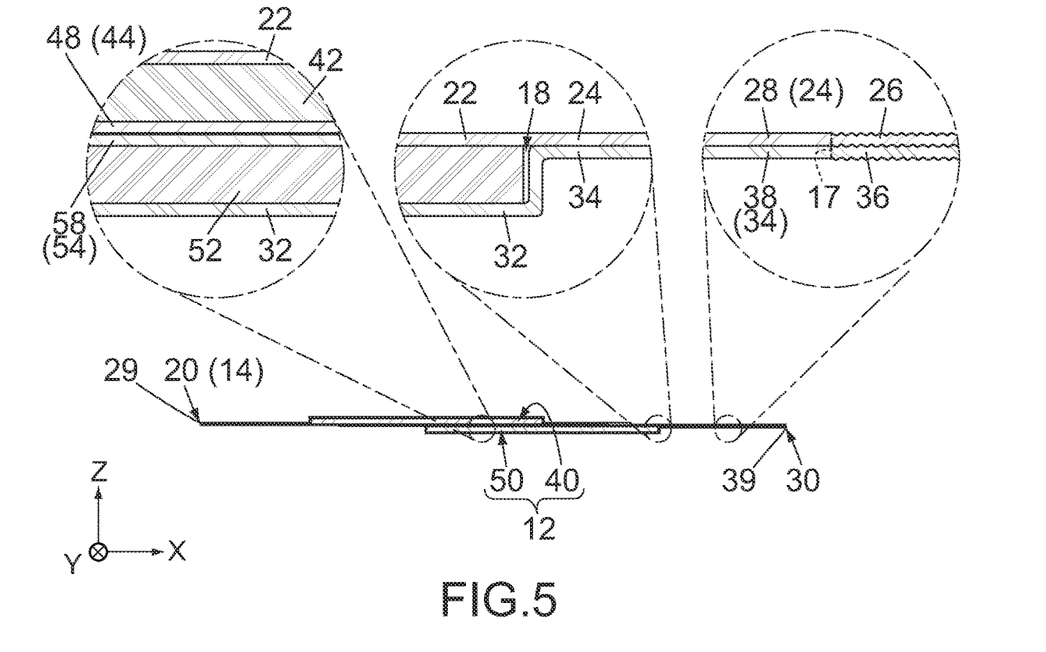
FIG. 5 is a cross-sectional view showing the device of FIG. 1, taken along line V-V, wherein three parts of the device each enclosed by chain dotted lines are enlarged and illustrated, and the boundary line of the contact region in one of the enlarged views is illustrated with dashed line.

Referring to FIGS. 1, 2 and 5, the first inner portion 22 of the first film 20 and the second inner portion 32 of the second film 30 of the device 10 are parts for accommodating the circuit structure 12. According to the present embodiment, before the device 10 is formed, the first film 20 extends uniformly along the XY-plane, and there is no visible boundary between the first inner portion 22 and the first outer portion 24. Before the device 10 is formed, the second film 30 extends uniformly along the XY-plane, and there is no visible boundary between the second inner portion 32 and the second outer portion 34. However, the present invention is not limited thereto. For example, a visible boundary such as a depression may be formed between the first inner portion 22 and the first outer portion 24, and a visible boundary such as a depression may be formed between the second inner portion 32 and the second outer portion 34.

Referring to FIG. 2, the first outer portion 24 has a first seal portion 26 and a first contact portion 28. The second outer portion 34 has a second seal portion 36 and a second contact portion 38. Referring to FIG. 1 together with FIG. 2, the first seal portion 26 and the second seal portion 36 are bonded together to form a seal trace 16. According to the present embodiment, the first seal portion 26 and the second seal portion 36 are bonded together by heat-sealing. Thus, the seal trace 16 of the present embodiment is a trace where the first seal portion 26 and the second seal portion 36 are welded to each other by heating. However, the present invention is not limited thereto, but the first seal portion 26 and the second seal portion 36 can be bonded together by various methods such as high frequency, ultrasonic or laser.

Referring to FIGS. 1 and 2, the seal trace 16 of the present embodiment is formed throughout entire circumference of the first seal portion 26 and the second seal portion 36. In other words, the seal trace 16 surrounds the first inner portion 22 and the second inner portion 32 throughout their entire circumference in the XY-plane. Meanwhile, a part of the first seal portion 26 and a part of the second seal portion 36, in particular, outer circumferences of the first seal portion 26 and the second seal portion 36 in the XY-plane, are not heat-sealed and thereby are not formed with the seal trace 16. However, the present invention is not limited thereto, but the seal trace 16 may be formed all over the first seal portion 26 and the second seal portion 36.

Referring to FIG. 1 together with FIG. 5, as described later, the first seal portion 26 and the second seal portion 36 are bonded together in a vacuumed environment. When the first seal portion 26 and the second seal portion 36 are bonded together, the first contact portion 28 and the second contact portion 38 are brought into contact with each other in a contact region 17 because of air pressure difference. The contact region 17 seamlessly surrounds the first inner portion 22 and the second inner portion 32 throughout their entire circumference in the XY-plane. As a result, the device 10 is formed with a closed space 18 which is enclosed by the first inner portion 22 and the second inner portion 32. According to the present embodiment, the first seal portion 26 and the second seal portion 36 are bonded together under a state where the air pressure in the closed space 18 is set to a low pressure which is close to that of a vacuum. In addition, the contact region 17 blocks the air which might flow between the inside and the outside of the closed space 18. Thus, the air pressure in the closed space 18 is kept to a low pressure lower than the atmospheric pressure.

Referring to FIG. 5, the first circuit member 40 and the second circuit member 50 are shut in the closed space 18 which is kept having the aforementioned low pressure. The first contact point 48 and the second contact point 58 are in contact with each other in the closed space 18. In detail, the first contact point 48 and the second contact point 58 are pressed against each other because of the air pressure difference between the inside and the outside of the closed space 18. Therefore, the contact between the first contact point 48 and the second contact point 58 can be securely kept even in an instance where each of the first contact point 48 and the second contact point 58 are not plated with material such as gold.

Summarizing the explanation described above, the first film 20 and the second film 30 of the device 10 of the present embodiment overlap with each other to be in contact with each other while the first circuit member 40 and the second circuit member 50 (hereafter, simply referred to as "circuit members") are sandwiched therebetween. The structure of each of the circuit members is not restricted except that each of the circuit members should be provided with a contact point such as the first contact point 48 or the second contact point 58. Thus, each of the circuit members of the present embodiment has a simple structure and can be formed of various material. For example, each of the circuit members may be an insulation film formed with a conductive pattern having a contact point, such as the first conductive pattern 44 or the second conductive pattern 54. In this instance, the thickness of the whole device 10 can be made extremely thin. Thus, the present embodiment provides the new device 10 which is new and can be made thinner.

Referring to FIGS. 2 and 5, the first seal portion 26 of the first film 20 and the second seal portion 36 of the second film 30 are parts for securely bonding the first film 20 and the second film 30 together by sealing such as heat-sealing. The first contact portion 28 of the first film 20 and the second contact portion 38 of the second film 30 are parts which are brought into contact with each other in accordance with the bonding of the first seal portion 26 and the second seal portion 36 under a low pressure. According to the present embodiment, there is no visible boundary between the first seal portion 26 and the first contact portion 28 before the sealing. Similarly, there is no visible boundary between the second seal portion 36 and the second contact portion 38 before the sealing. However, the present invention is not limited thereto. For example, a visible boundary such as a depression may be formed between the first seal portion 26 and the first contact portion 28, and a visible boundary such as a depression may be formed between the second seal portion 36 and the second contact portion 38.

According to the present embodiment, the first contact portion 28 and the second contact portion 38 seamlessly surround the first inner portion 22 and the second inner portion 32 throughout their entire circumference in the XY-plane. The first seal portion 26 and the second seal portion 36 seamlessly surround the first contact portion 28 and the second contact portion 38 throughout their entire circumference in the XY-plane. According to this structure, the closed space 18 can be reliably kept airtight. Moreover, the first circuit member 40 and the second circuit member 50 can be easily taken out from the closed space 18 by cutting off the first seal portion 26 and the second seal portion 36. Thus, according to the present embodiment, the members can be easily collected separately and can be reused. However, the present invention is not limited thereto. For example, the first seal portion 26 and the second seal portion 36 may partially surround the first contact portion 28 and the second contact portion 38 in the XY-plane. Moreover, the first seal portion 26 and the second seal portion 36 may be partially surrounded by the first contact portion 28 and the second contact portion 38.

Figure 8:
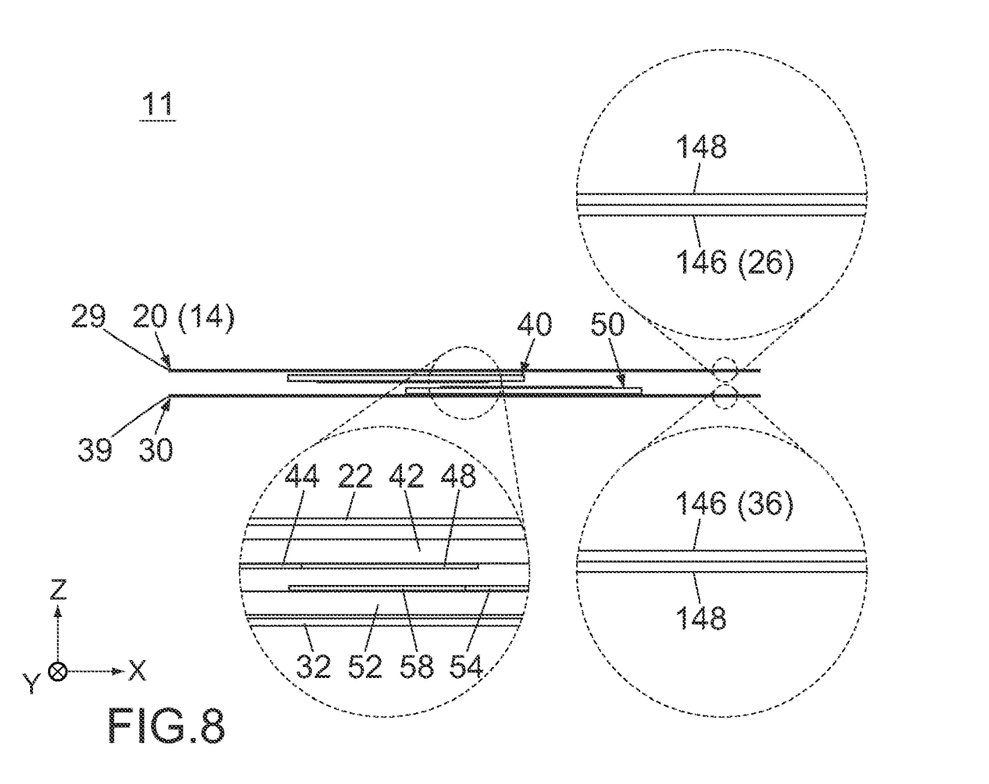
FIG. 8 is a side view showing the device material set of FIG. 7, wherein three parts of the device material set enclosed by dashed line are enlarged and illustrated.

Referring to FIGS. 1 and 8, each of the first film 20 and the second film 30 of the present embodiment includes two layers consisting of a meltable layer 146 which is meltable by the heat-sealing and an unmeltable layer 148 which is not meltable by the heat-sealing. In other words, each of the first film 20 and the second film 30 has a two-layer structure formed of the meltable layer 146 and the unmeltable layer 148. For example, the meltable layer 146 is made of polyethylene, and the unmeltable layer 148 is made of nylon. According to this structure, the meltable layers 146 can be fused to each other while the unmeltable layers 148 of the first seal portion 26 and the second seal portion 36 are maintained. However, the present invention is not limited thereto, but each of the first film 20 and the second film 30 may have a structure in accordance with the sealing method. For example, each of the first film 20 and the second film 30 may include only one layer or may include three or more layers.

Each of the first film 20 and the second film 30 of the present embodiment is formed so that a part thereof, which is other than the first seal portion 26 and the second seal portion 36, also includes the meltable layer 146 and the unmeltable layer 148. However, the present invention is not limited thereto. For example, the meltable layer 146 may be formed only in each of the first seal portion 26 and the second seal portion 36.

Referring to FIG. 1, each of the first film 20 and the second film 30 is preferred to have a high barrier property against oxygen. More specifically, each of the first film 20 and the second film 30 is preferred to comprise a layer made of high oxygen barrier material which is material having a high barrier property against oxygen. According to this layer-structure, oxidation of the metal members of the circuit structure 12 can be reduced.

For example, the high oxygen barrier material may be linear low-density polyethylene (LLDPE). More specifically, the high oxygen barrier material may be PET/Al/PE which is formed by laminating polyethylene terephthalate, aluminum and polyethylene; ON/PE which is formed by laminating biaxially stretched nylon and polyethylene; PET/EVOH/PE which is formed by laminating polyethylene terephthalate, polyvinyl chloride and polyethylene; or may be formed by laminating a transparent high barrier film and polyethylene. The transparent high barrier film may be polyethylene terephthalate (PET) deposited with SiOx or aluminum oxide.

Each of the first film 20 and the second film 30 of the present embodiment is preferred to have a high barrier property against water vapor in addition to the high barrier property against oxygen. More specifically, each of the first film 20 and the second film 30 is preferred to comprise a layer made of high water-vapor barrier material which is material having a high barrier property against water vapor. According to this layer-structure, the circuit structure 12 can be water-proofed. For example, the high water-vapor barrier material may be material which is a sheet made of ON/PE, biaxially stretched polypropylene (OPP) or PET and is coated with polyvinylidene chloride (PVDC).

Each of the first film 20 and the second film 30 may have various barrier properties such as a barrier property against nitrogen in addition to the high barrier property against oxygen and the high barrier property against water vapor. Thus, each of the first film 20 and the second film 30 is preferred to have high barrier properties in accordance with its use.

Figure 6:
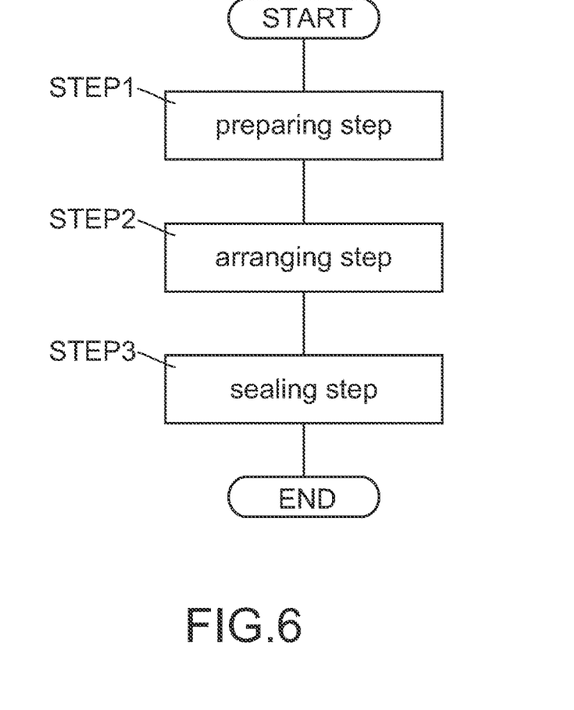
FIG. 6 is a flowchart showing an example of a forming method for forming the device of FIG. 1.

Referring to FIG. 6, the device 10 (see FIG. 1) of the present embodiment is formed via three steps consisting of a preparing step (STEP 1), an arranging step (STEP 2) and a sealing step (STEP 3). However, the present invention is not limited thereto, but the forming method of the device 10 can be modified as necessary. Hereafter, explanation will be made about the forming method of the device 10 of the present embodiment.

Figure 7:
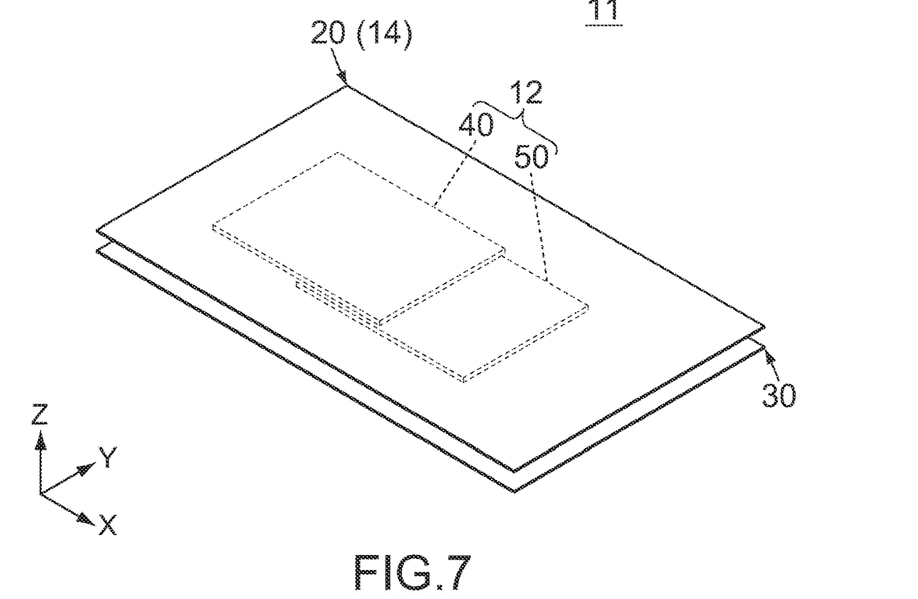
FIG. 7 is a perspective view showing a device material set which is prepared in a preparing step of the forming method of FIG. 6, wherein outlines of a hidden first circuit member and a hidden second circuit member are illustrated with dashed line.

Referring to FIG. 7, in the preparing step (see FIG. 6), a device material set 11 is prepared. The device material set 11 comprises the first film 20, the second film 30, the first circuit member 40 and the second circuit member 50. Referring to FIG. 8, as previously described, the first circuit member 40 comprises the first contact point 48, and the second circuit member 50 comprises the second contact points 58. Thus, the forming method of the present embodiment comprises preparing the first film 20, the second film 30, the first circuit member 40 and the second circuit member 50, the first circuit member 40 comprising the first contact point 48, the second circuit member 50 comprising the second contact points 58.

Then, in the arranging step (see FIG. 6), the first film 20, the first circuit member 40, the second circuit member 50 and the second film 30 are stacked on each other in this order from top to bottom along the Z-direction. Meanwhile, the first circuit member 40 and the second circuit member 50 are located at the middle of the first film 20 and the second film 30 in the XY-plane. In addition, the first circuit member 40 and the second circuit member 50 are arranged so that the first contact point 48 and the second contact point 58 face each other in the Z-direction. In addition, the first film 20 and the second film 30 are arranged so that two of the meltable layers 146 thereof face each other in the Z-direction.

Figure 9:
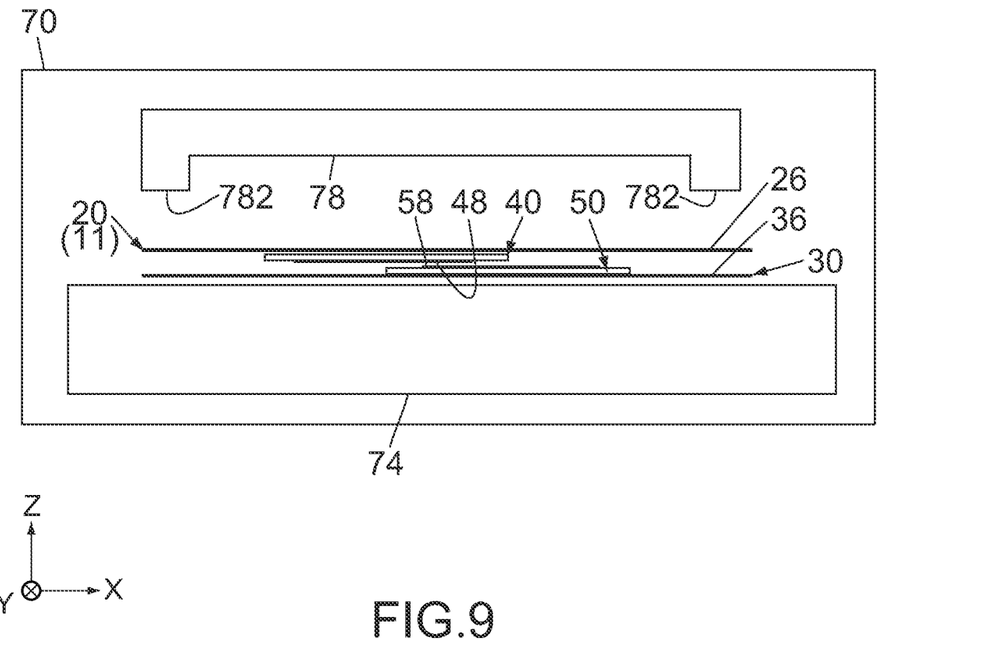
FIG. 9 is a view showing a schematic structure of a chamber and a side of the device material set arranged in the chamber in an arranging step of the forming method of FIG. 6.

Then, referring to FIG. 9, the device material set 11 which is arranged as described above is accommodated in a chamber 70. Thus, the forming method of the present embodiment comprises arranging the first film 20, the first circuit member 40, the second circuit member 50 and the second film 30, which are stacked in this order, in the chamber 70 while the first contact point 48 and the second contact point 58 face each other.

The chamber 70 is a device capable of making its inside space extremely close to a vacuum. The chamber 70 of the present embodiment comprises a die 74 and a heat-seal bar 78. The device material set 11 is placed on the die 74. Thereafter, the first film 20 and the second film 30 are sealed as the air pressure of the inside space of the chamber 70 is lowered.

In detail, the heat-seal bar 78 of the present embodiment has a heating portion 782. According to the present embodiment, the heating portion 782 is heated so as to have a temperature higher than the melting point of the meltable layer 146 (see FIG. 8). The thus-heated heating portion 782 is pressed against the first seal portion 26 of the first film 20 and the second seal portion 36 of the second film 30 which vertically overlap with each other so that the first seal portion 26 and the second seal portion 36 are heat-sealed. As a result, the first circuit member 40 and the second circuit member 50 are shut in the closed space 18 (see FIG. 5) which is enclosed by the first film 20 and the second film 30. Meanwhile, the first contact point 48 and the second contact point 58 are brought into contact with each other.

Thus, the forming method of the present embodiment comprises sealing the first film 20 and the second film 30 under a state where the chamber 70 is vacuumed, so that the first circuit member 40 and the second circuit member 50 are shut in the closed space 18 (see FIG. 5) enclosed by the first film 20 and the second film 30, and the first contact point 48 and the second contact point 58 are brought into contact with each other.

According to the sealing step of the present embodiment, the first film 20 and the second film 30 are heat-sealed under a low pressure close to that of a vacuum. According to this forming method, the first contact point 48 and the second contact point 58 are securely in contact with each other without using a fixing member such as an adhesive. Therefore, when the device 10 (see FIG. 1) is no longer used, the device 10 can be disassembled merely by cutting off the first seal portion 26 and the second seal portion 36. In addition, the first circuit member 40 and the second circuit member 50 can be shut in the closed space 18 (see FIG. 5) having a low pressure, so that degradation of the metal members due to oxidation can be reduced, for example. However, the present invention is not limited thereto, but the forming method and the sealing method of the device 10 can be modified as necessary.

Figure 10:
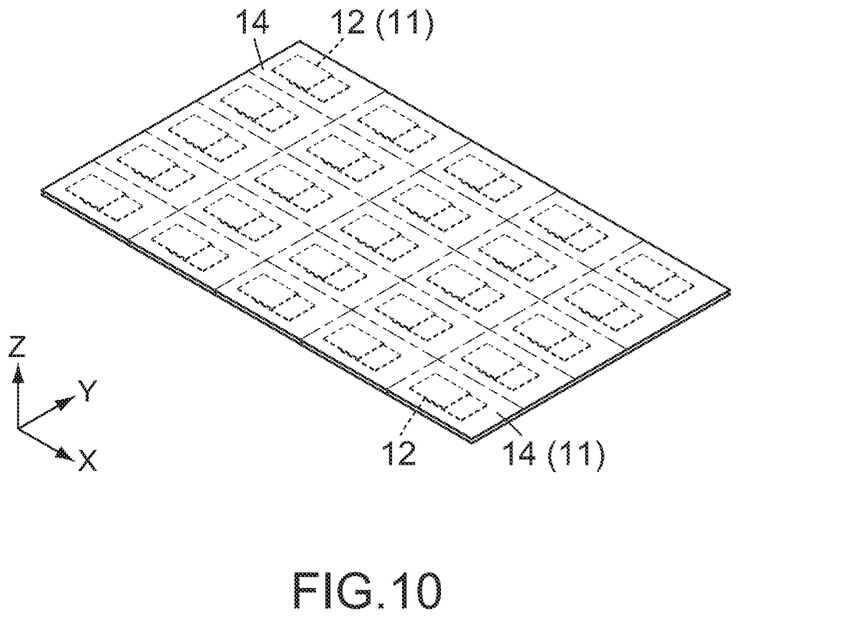
FIG. 10 is a view showing a member comprising a plurality of the device material sets of FIG. 7, wherein outlines of the hidden first circuit members and the hidden second circuit members are illustrated with dashed line, and boundary lines between every one of the device material sets and the others are illustrated with chain dotted lines.

Referring to FIGS. 6 to 9, according to the aforementioned forming method, one of the device 10 (see FIG. 1) is formed from one of the device material set 11 via the steps from the preparing step to the sealing step. However, the present invention is not limited thereto. For example, referring to FIG. 10, a member comprising a plurality of the device material sets 11 may be prepared and arranged. The sealing step (see FIGS. 6 and 9) may be performed to this whole member. Moreover, the member illustrated in FIG. 10 may be moved into the chamber 70 (see FIG. 9) by a device such as a roller.

The present embodiment can be further variously modified in addition to the already described modifications. Hereafter, explanation will be made about two modifications.

Figure 11:
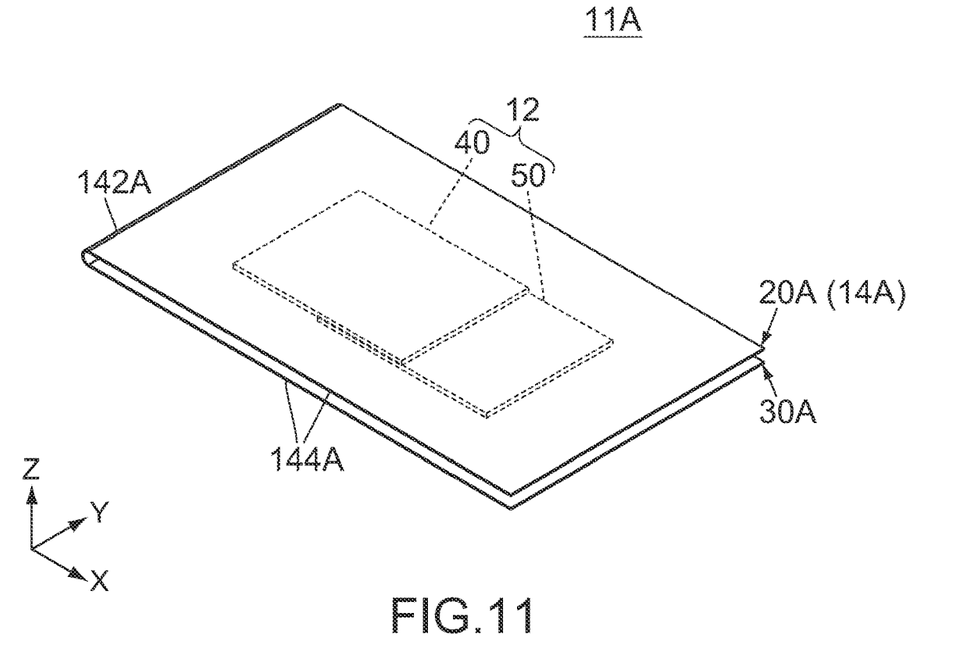
FIG. 11 is a perspective view showing a modification of the device material set of FIG. 7, wherein outlines of a hidden first circuit member and a hidden second circuit member are illustrated with dashed line.
Figure 12:
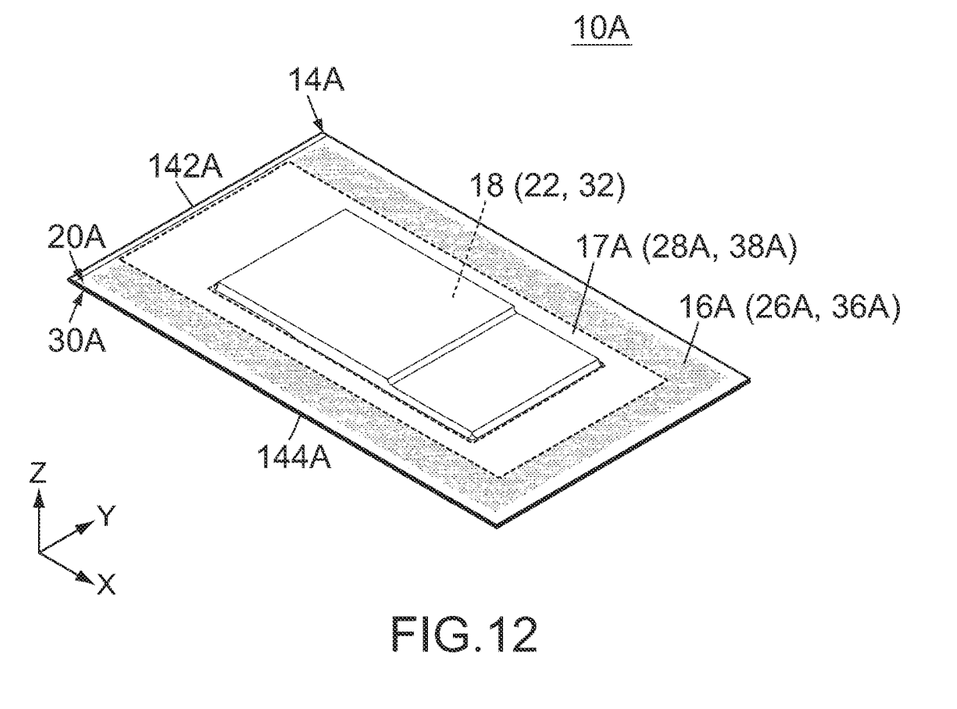
FIG. 12 is a perspective view showing a device formed of the device material set of FIG. 11, wherein boundary lines of a contact region formed between a first film and a second film are illustrated with dashed line.

Referring to FIGS. 11 and 12, a device 10A according to a modification of the present embodiment is formed from a device material set 11A. Referring to FIG. 11, the device material set 11A comprises the circuit structure 12 same as that of the device material set 11 and comprises one planar sheet 14A made of insulator instead of the first film 20 (see FIG. 7) and the second film 30 (see FIG. 7) of the device material set 11 (see FIG. 7). The circuit structure 12 comprises the first circuit member 40 and the second circuit member 50.

The planar sheet 14A is bent at the middle thereof, namely a predetermined portion 142A, in a front-rear direction (X-direction) so as to form a first film (sheet piece) 20A and a second film (sheet piece) 30A which overlap with each other in the Z-direction. Thus, the first film 20A and the second film 30A are two sheet pieces of the single film member 14A which overlap with each other. The film member 14A is a single planar sheet. The film member 14A has the predetermined portion 142A and a cutting edge 144A. The cutting edge 144A is an edge of the film member 14A in the XY-plane.

The device 10A of the present modification can be formed by a forming method similar to that of the device 10 (see FIG. 1). For example, in the arranging step (see FIG. 6), the circuit structure 12 is arranged between the first film 20A and the second film 30A in the Z-direction.

Referring to FIG. 12, the device 10A has a structure similar to that of the device 10 (see FIG. 1). For example, a first seal portion 26A and a second seal portion 36A are bonded together to form a seal trace 16A. A first contact portion 28A and a second contact portion 38A are in contact with each other in a contact region 17A. The contact region 17A surrounds the first inner portion 22 and the second inner portion 32 throughout their entire circumference. The device 10A is formed with the closed space 18 which is enclosed by the first inner portion 22 and the second inner portion 32. The first circuit member 40 (see FIG. 10) and the second circuit member 50 (see FIG. 10) are shut in the closed space 18. The first contact point 48 (see FIG. 3) of the first circuit member 40 and the second contact point 58 (see FIG. 3) of the second circuit member 50 are in contact with each other.

However, the device 10A is different from the device 10 (see FIG. 1) in the following points. First, the first film 20A and the second film 30A are two of the sheet pieces which are folded at the predetermined portion 142A to overlap with each other. Thus, the first film 20A and the second film 30A are connected to each other at the predetermined portion 142A. According to this structure, there is no need to seal the part between the predetermined portion 142A and the contact region 17A. Accordingly, only the part between the contact region 17A and the cutting edge 144A is sealed. In other words, the seal trace 16A is formed only between the contact region 17A and the cutting edge 144A. However, the present invention is not limited thereto, but the part between the predetermined portion 142A and the contact region 17A may be sealed. Thus, the seal trace 16A should be formed at least between the contact region 17A and the cutting edge 144A.

Figure 13:
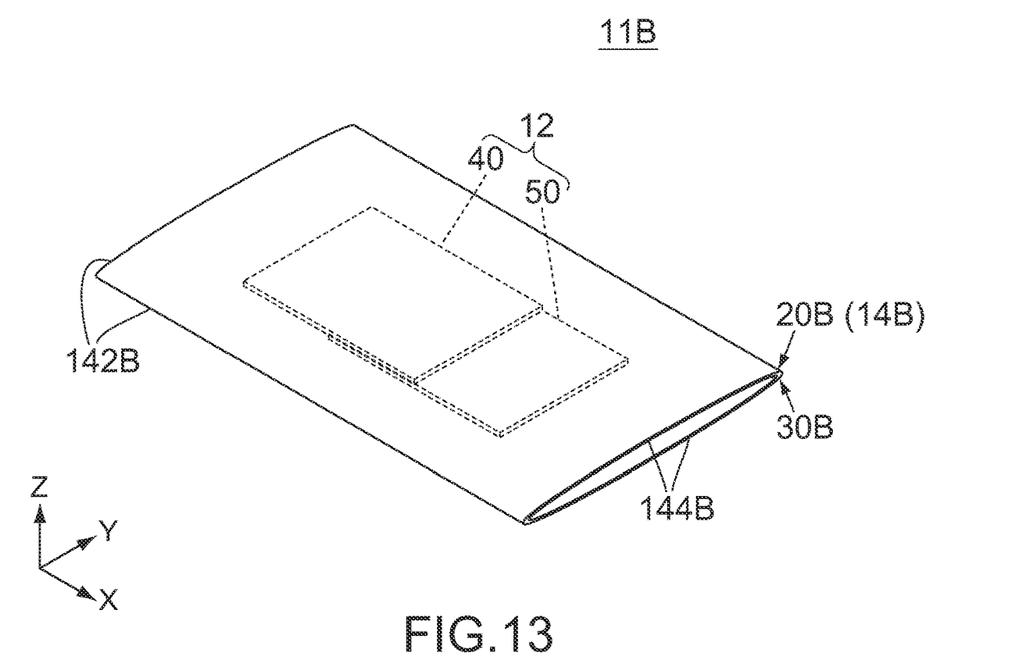
FIG. 13 is a perspective view showing another modification of the device material set of FIG. 7, wherein outlines of a hidden first circuit member and a hidden second circuit member are illustrated with dashed line.
Figure 14:
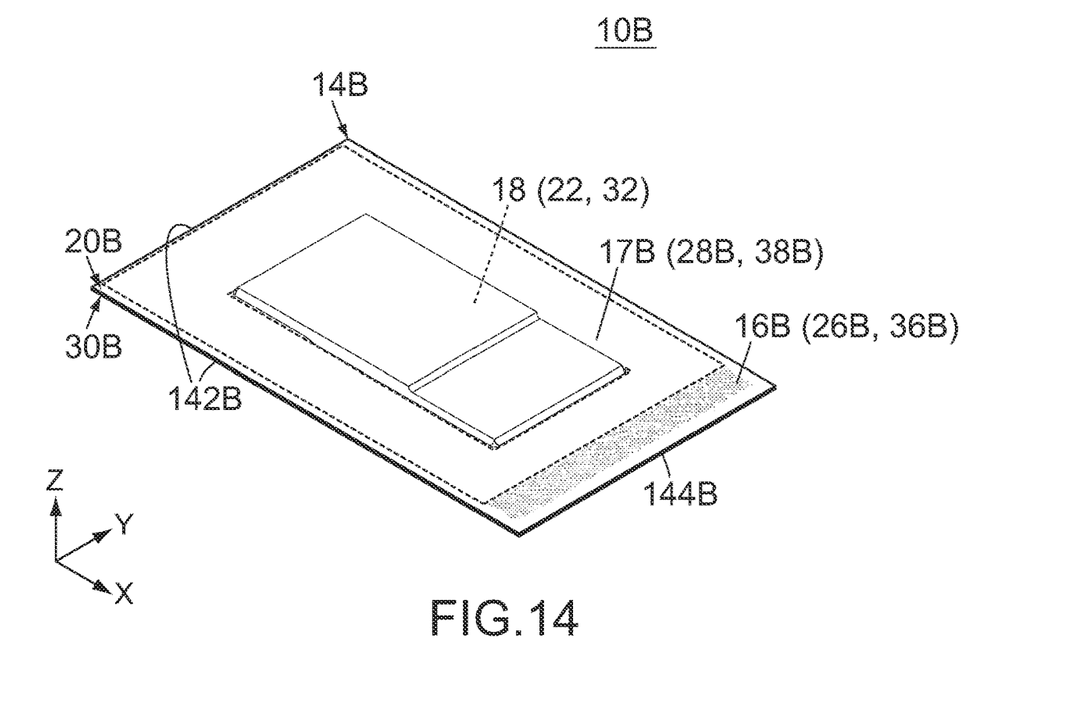
FIG. 14 is a perspective view showing a device formed of the device material set of FIG. 13, wherein boundary lines of a contact region formed between a first film and a second film are illustrated with dashed line.

Referring to FIGS. 13 and 14, a device 10B according to another modification of the present embodiment is formed from a device material set 11B. Referring to FIG. 13, the device material set 11B comprises the circuit structure 12 same as that of the device material set 11 and comprises one folder-like sheet 14B made of insulator instead of the first film 20 (see FIG. 7) and the second film 30 (see FIG. 7) of the device material set 11 (see FIG. 7). The circuit structure 12 comprises the first circuit member 40 and the second circuit member 50.

The folder-like sheet 14B has three connected sides, namely a predetermined portion 142B, in the XY-plane and opens at a front end (positive X-side end) thereof. According to this structure, the folder-like sheet 14B is formed with a first film (sheet piece) 20B and a second film (sheet piece) 30B which overlap with each other in the Z-direction. Thus, the first film 20B and the second film 30B are two sheet pieces of the single film member 14B which overlap with each other. The film member 14B is a single folder-like sheet. The film member 14B has the predetermined portion 142B and a cutting edge 144B. The cutting edge 144B is the edge of the opening of the film member 14B.

The device 10B of the present modification can be formed by a forming method similar to that of the device 10 (see FIG. 1). For example, in the arranging step (see FIG. 6), the circuit structure 12 is put into the film member 14B and is arranged between the first film 20B and the second film 30B in the Z-direction.

Referring to FIG. 14, the device 10B has a structure similar to that of the device 10 (see FIG. 1). For example, a first seal portion 26B and a second seal portion 36B are bonded together to form a seal trace 16B. A first contact portion 28B and a second contact portion 38B are in contact with each other in a contact region 17B. The contact region 17B surrounds the first inner portion 22 and the second inner portion 32 throughout their entire circumference. The device 10B is formed with the closed space 18 which is enclosed by the first inner portion 22 and the second inner portion 32. The first circuit member 40 (see FIG. 12) and the second circuit member 50 (see FIG. 12) are shut in the closed space 18. The first contact point 48 (see FIG. 3) of the first circuit member 40 and the second contact point 58 (see FIG. 3) of the second circuit member 50 are in contact with each other.

However, the device 10B is different from the device 10 (see FIG. 1) in the following points. First, the first film 20B and the second film 30B are two of the sheet pieces which are connected to each other at the predetermined portion 142B. Thus, the first film 20B and the second film 30B are connected to each other at the predetermined portion 142B. According to this structure, there is no need to seal the part between the predetermined portion 142B and the contact region 17B. Accordingly, only the part between the contact region 17B and the cutting edge 144B is sealed. In other words, the seal trace 16B is formed only between the contact region 17B and the cutting edge 144B. However, the present invention is not limited thereto, but the part between the predetermined portion 142B and the contact region 17B may be sealed. Thus, the seal trace 16B should be formed at least between the contact region 17B and the cutting edge 144B.

In the aforementioned two modifications, the film member is one planar sheet or one folder-like sheet. However, the film member according to the present invention is not limited thereto but can be variously modified.

Referring to FIG. 1, the device 10 can be further variously modified in addition to the already described modifications. For example, as previously described, the device 10 may further comprise another member in addition to the four members, i.e., the first film 20, the second film 30, the first circuit member 40 and the second circuit member 50. Hereafter, explanation will be made about a modification in which the device 10 comprises the other members.

Figure 15:
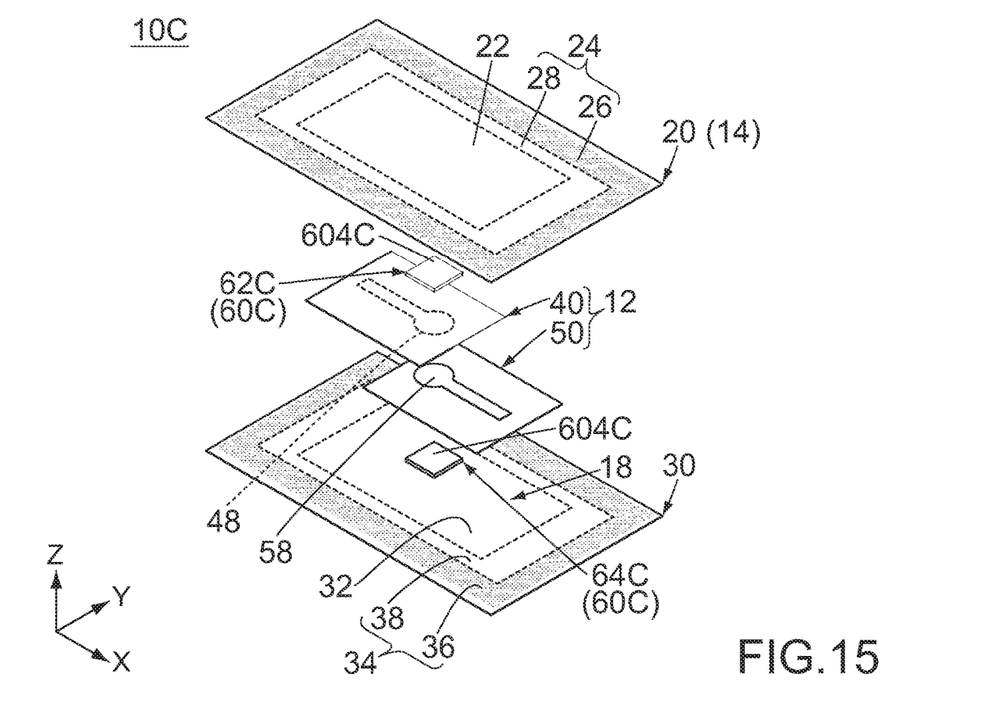
FIG. 15 is an exploded, perspective view showing a modification of the device of FIG. 2, wherein outlines of a hidden first conductive pattern is illustrated with dashed line.
Figure 16:
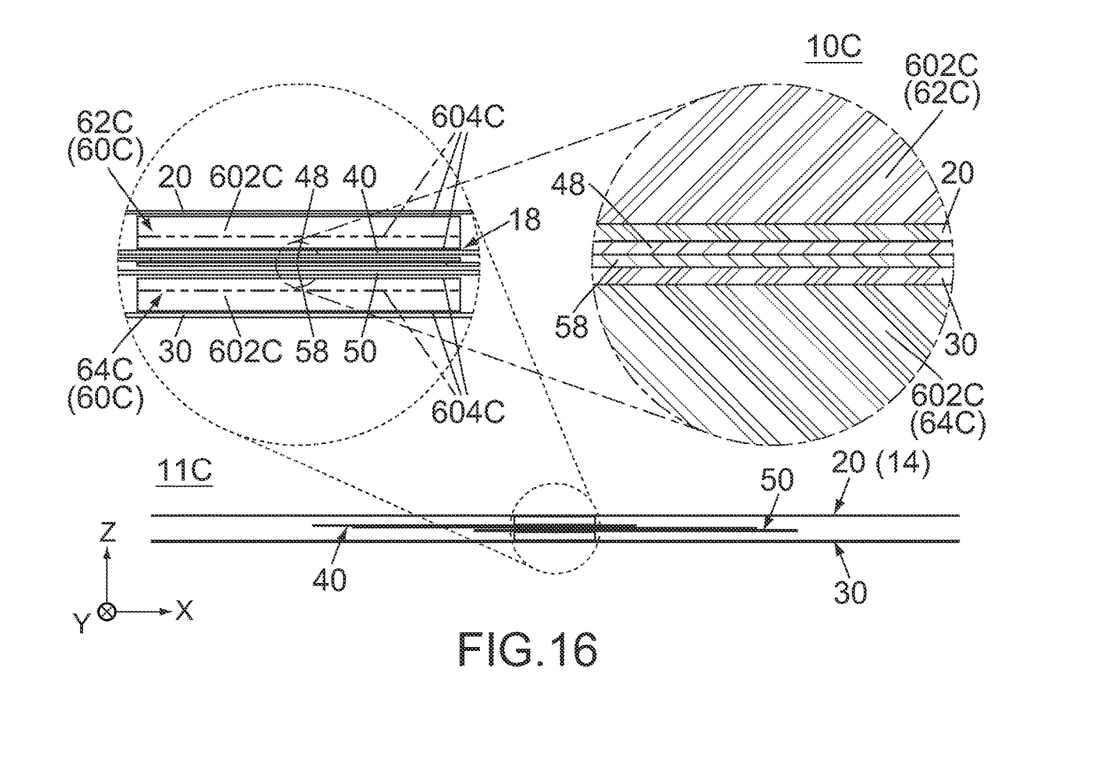
FIG. 16 is a side view showing a device material set of the device of FIG. 15, wherein a part of the device material set enclosed by dashed line is enlarged and illustrated, positions of main surfaces of an compressed elastic member in the enlarged view are illustrated with two-dot chain line, a part of the enlarged view enclosed by chain dotted lines is further enlarged, and a cross-section of the fabricated device is illustrated in the further enlarged view.

Comparing FIG. 15 with FIG. 2, a device 10C of the present modification comprises two elastic members 60C, which the device 10 does not comprise, in addition to the first film 20, the second film 30, the first circuit member 40 and the second circuit member 50 same as those of the device 10. The elastic members 60C of the present modification include a first elastic member 62C and a second elastic member 64C. Referring to FIGS. 15 and 16, the elastic members 60C are shut in the closed space 18 (see FIG. 5) together with the first circuit member 40 and the second circuit member 50. The first elastic member 62C is located between the first film 20 and the first contact point 48 in the Z-direction. The second elastic member 64C is located between the second film 30 and the second contact point 58 in the Z-direction.

Referring to FIG. 15, each of the elastic members 60C of the present modification is a foaming, cushioning material having elasticity. More specifically, each of the elastic members 60C of the present modification is an open-cell structure such as a urethane sponge, a polyolefin sponge or a chloroprene rubber (CR) sponge. The open-cell structure of the present modification is formed of an expansible and compressible elastic body and a large number of cells which are densely formed in the elastic body. The cells are connected to each other to form open cells. The open cells open outward from the elastic body. When the open-cell structure is compressed, the open-cell structure shrinks while the air in the cells is discharged. When the compression of the open-cell structure is stopped, the open-cell structure expands to restore its shape before the compression while the outside air is absorbed into the cells. Each of the elastic members 60C of the present modification is an excellent cushioning material made of such open-cell structure.

Referring to FIGS. 15 and 16, each of the elastic members 60C of the present modification has a body 602C and two main surfaces 604C. Two of the main surfaces 604C of each of the elastic members 60C are located opposite to each other in a predetermined direction, or in the Z-direction in FIGS. 15 and 16, across the body 602C and extend in parallel to each other along a plane perpendicular to the predetermined direction, or along the XY-plane in FIGS. 15 and 16. For each of the elastic members 60C, when the body 602C is compressed so that two of the main surfaces 604C are close to each other in the predetermined direction, a part of the air contained in the body 602C is discharged, and when the compressing of the body 602C is stopped, air flows into the body 602C.

Referring to FIG. 15 together with FIG. 1, the device 100 is formed similarly to the device 10. In detail, referring to FIG. 6 together with FIGS. 1 and 15, the device 100 is formed via three steps consisting of the preparing step (STEP 1), the arranging step (STEP 2) and the sealing step (STEP 3) similarly to the device 10. Hereafter, explanation will be made about the forming method of the device 100 of the present modification. The explanation will be made mainly about difference from the forming method of the device 10.

Comparing FIG. 16 with FIG. 8, in the preparing step (see FIG. 6) of the present modification, a device material set 110 is prepared. The device material set 11C comprises two of the elastic members 60C including the first elastic member 62C and the second elastic member 64C, which the device material set 11 does not comprise, in addition to the first film 20, the second film 30, the first circuit member 40 and the second circuit member 50 same as those of the device material set 11.

Then, in the arranging step (see FIG. 6) of the present modification, the first film 20, the first elastic member 62C, the first circuit member 40, the second circuit member 50, the second elastic member 64C and the second film 30 are stacked on each other in this order from top to bottom along the Z-direction. Meanwhile, the first elastic member 62C is arranged between the first film 20 and the first circuit member 40 in the Z-direction so as to be located just over the first contact point 48. In addition, the second elastic member 64C is arranged between the second film 30 and the second circuit member 50 in the Z-direction so as to be located just under the second contact points 58.

Then, referring to FIG. 9 together with FIG. 16, the device material set 11C which is arranged as described above is accommodated in the chamber 70. The device material set 110 is placed on the die 74. Thereafter, the sealing step similar to the sealing step (see FIG. 6) of the device 10 (see FIG. 1) is performed. More specifically, the first film 20 and the second film 30 are heat-sealed while the air pressure of the inside space of the chamber 70 is lowered by vacuum drawing. As a result, the first circuit member 40, the second circuit member 50 and the elastic members 60C are shut in the closed space 18 (see FIG. 16) which is enclosed by the first film 20 and the second film 30. Meanwhile, the first contact point 48 and the second contact point 58 are brought into contact with each other.

Referring to FIG. 16, in the sealing step (see FIG. 6), as the air pressure of the inside space of the chamber 70 (see FIG. 9) is lowered, the first film 20 presses the first elastic member 62C against a part of the first circuit member 40 located just behind the first contact point 48, and the second film 30 presses the second elastic member 64C against a part of the second circuit member 50 located just behind the second contact points 58. As a result, each of the elastic members 60C is compressed mainly in the predetermined direction (Z-direction) while the air in the body 602C is discharged (see the positions of the main surfaces 604C after the compression which are illustrated with two-dot chain line in the enlarged view of FIG. 16). Therefore, the thickness, or a size in the Z-direction, of each of the elastic members 60C of the device 10C is extremely thin. Thus, the present modification provides the device 10C which is new and can be made thinner.

The first contact point 48 of the device 10C is pressed against the second contact points 58 by the restoring force of the compressed first elastic member 62C. The second contact points 58 is pressed against the first contact point 48 by the restoring force of the compressed second elastic member 64C. According to the present modification, the first contact point 48 and the second contact point 58 can be further stably connected to each other by two of the elastic members 60C which are arranged so that the first contact point 48 and the second contact point 58 are sandwiched and pressed therebetween.

Even if air flows into the closed space 18 of the device 10C in use, the air is absorbed into the elastic members 60C. In this situation, since the restoring force of each of the elastic members 60C is only slightly reduced, the change in contact force between the first contact point 48 and the second contact point 58 can be reduced. Moreover, the device 10C comprising the elastic members 60C is hardly damaged even when being bent. The present modification provides the device 10C which can stably work for a long time under various environments.

The present modification can be further variously modified as described below.

Referring to FIG. 15, each of the elastic members 60C has a rectangular flat-plate shape. The size of each of the elastic members 60C in the XY-plane is about same as the size of each of the first contact point 48 and the second contact point 58 in the XY-plane. However, the present invention is not limited thereto. For example, the shape of each of the elastic members 60C is not specifically limited. The size of each of the elastic members 60C in the XY-plane is not specifically limited, provided that the elastic members 60C can be shut in the closed space 18 (see FIG. 5) so that the first contact point 48 and the second contact point 58 are pressed against each other. Thus, the first elastic member 62C should be, at least in part, located between the first film 20 and the first contact point 48, and the second elastic member 64C should be, at least in part, located between the second film 30 and the second contact point 58.

For example, the size of each of the elastic members 60C in the XY-plane may be about same as the size of each of the first circuit member 40 and the second circuit member 50 in the XY-plane. In an instance where the size of each of the elastic members 60C is made large as described above, the expansion of the elastic members 60C can be reduced even when air flows into the closed space 18. In addition, the elastic members 60C each having a large size can be easily arranged in the arranging step (see FIG. 6) so as to correspond to the first contact point 48 and the second contact point 58. In particular, even when each of the number of the first contact points 48 and the number of the second contact points 58 is two or more, the elastic members 60C each having a large size can be easily arranged in the arranging step without increasing the number of the elastic members 60C.

The elastic members 60C of the present modification includes both of the first elastic member 62C and the second elastic member 64C. However, the present invention is not limited thereto. For example, the elastic members 60C may include only one of the first elastic member 62C and the second elastic member 64C. Instead, each of the number of the first elastic members 62C and the number of the second elastic members 64C may be two or more. Thus, the device 10C should comprise one or more of the elastic members 60C. The elastic members 60C may include at least one of the first elastic member 62C and the second elastic member 64C.

Each of the elastic members 60C may be formed of material other than the open-cell structure. For example, each of the elastic members 60C may be formed of a closed-cell structure which includes a large number of cells independent from each other so as to work similarly to the open-cell structure. More specifically, the closed-cell structure may be formed of a hole which opens outward so that the air in the hole is discharged upon compression. Each of the elastic members 60C may be formed of two flat plates which are connected to each other by a large number of springs so as to work similarly to the open-cell structure. Moreover, each of the elastic members 60C may be formed of an elastic body such as rubber which contains none of the cells. However, when each of the elastic members 60C is formed of an elastic body which contains no open cell, the part which is elastically deformed upon compression might be unbalanced so that the first contact point 48 or the second contact point 58 cannot be entirely and uniformly pressed. Therefore, from the viewpoint of stable connection between the first contact point 48 and the second contact point 58, each of the elastic members 60C is preferred to be formed of the open-cell structure.

Referring to FIG. 15 together with FIGS. 1, 12 and 14, the device 10C of the present modification can be modified similarly to the device 10, the device 10A and the device 10B which are previously described. For example, the film member 14 of the device 10C may be one planar sheet or may be one folder-like sheet. The forming method of the device 10C can be also modified similarly to the forming method of the device 10 (see FIG. 10, for example).

While there has been described what is believed to be the preferred embodiment of the invention, those skilled in the art will recognize that other and further modifications may be made thereto without departing from the spirit of the invention, and it is intended to claim all such embodiments that fall within the true scope of the invention.

What is claimed is:

1. A device comprising a first film, a second film, a first circuit member and a second circuit member, wherein:
   the first film has a first inner portion and a first outer portion;
   the first inner portion is located inward of the first outer portion;
   the second film has a second inner portion and a second outer portion;
   the second inner portion is located inward of the second outer portion;
   the first outer portion has a first seal portion and a first contact portion;
   the second outer portion has a second seal portion and a second contact portion;
   the first seal portion and the second seal portion are bonded together to form a seal trace;
   the first contact portion and the second contact portion are in contact with each other in a contact region;
   the contact region surrounds the first inner portion and the second inner portion throughout their entire circumference;
   the device is formed with a closed space which is enclosed by the first inner portion and the second inner portion;
   the first circuit member and the second circuit member are shut in the closed space;
   the first circuit member comprises a first contact point;
   the second circuit member comprises a second contact point; and
   the first contact point and the second contact point are in contact with each other.

2. The device as recited in claim 1, wherein the first seal portion and the second seal portion are bonded together by heat-sealing.

3. The device as recited in claim 2, wherein each of the first film and the second film includes two layers consisting of a meltable layer which is meltable by the heat-sealing and an unmeltable layer which is not meltable by the heat-sealing.

4. The device as recited in claim 1, wherein:
   the first film and the second film are two sheet pieces of a single film member which overlap with each other;
   the film member has a predetermined portion and a cutting edge;
   the first film and the second film are connected to each other at the predetermined portion; and
   the seal trace is formed at least between the contact portion and the cutting edge.

5. The device as recited in claim 4, wherein:
   the film member is a single planar sheet; and
   the first film and the second film are the two sheet pieces which are folded at the predetermined portion to overlap with each other.

6. The device as recited in claim 4, wherein:
   the film member is a single folder-like sheet; and
   the first film and the second film are the two sheet pieces which are connected to each other at the predetermined portion.

7. The device as recited in claim 1, wherein:
   the first circuit member has a first base portion and a first conductive pattern;
   the first base portion is formed of an insulation film;
   the first conductive pattern is formed on the first base portion and has the first contact point;
   the second circuit member has a second base portion and a second conductive pattern;
   the second base portion is formed of an insulation film; and
   the second conductive pattern is formed on the second base portion and has the second contact point.

8. The device as recited in claim 1 wherein each of the first film and the second film has a high barrier property.

9. The device as recited in claim 8 wherein each of the first film and the second film has a high barrier property against oxygen.

10. The device as recited in claim 8 wherein each of the first film and the second film has a high barrier property against water vapor.

11. The device as recited in claim 1 wherein:
the device comprises one or more elastic members;
the elastic members are shut in the closed space; and
the one or more elastic members include at least one of a first elastic member that is, at least in part, located between the first film and the first contact point, and a second elastic member that is, at least in part, located between the second film and the second contact point.

12. The device as recited in claim 11 wherein:
each of the one or more elastic members has a body and two main surfaces;
the two main surfaces are located opposite to each other in a predetermined direction across the body; and
for each of the one or more elastic members, when the body is compressed so that the two main surfaces are close to each other in the predetermined direction, a part of air contained in the body is discharged, and when compressing of the body is stopped, air flows into the body.

13. The device as recited in claim 12 wherein each of the one or more elastic members is an open-cell structure.

* * * * *